United States Patent [19]
Sugihara et al.

[11] Patent Number: 6,151,519
[45] Date of Patent: *Nov. 21, 2000

[54] PLANAR ELECTRODE

[75] Inventors: Hirokazu Sugihara, Katano; Makoto Taketani, Kyoto; Tadayasu Mitsumata, Hirakata, all of Japan

[73] Assignee: Matsushita Electric Industrial Co., Ltd., Osaka, Japan

[ * ] Notice: This patent is subject to a terminal disclaimer.

[21] Appl. No.: 09/160,252

[22] Filed: Sep. 22, 1998

Related U.S. Application Data

[63] Continuation of application No. 08/481,149, Jun. 7, 1995, Pat. No. 5,810,725, which is a continuation-in-part of application No. 08/114,634, Sep. 2, 1993, abandoned.

[30] Foreign Application Priority Data

Apr. 16, 1993 [JP] Japan ................................. 5-090291

[51] Int. Cl.$^7$ ...................................... A61B 5/04
[52] U.S. Cl. ...................... 600/372; 600/373; 607/116; 204/403; 435/287.1
[58] Field of Search ................... 600/372, 373; 607/116, 117, 148; 204/403; 435/287.1

[56] References Cited

U.S. PATENT DOCUMENTS 5,810,725  9/1998  Sugihara et al. .................. 600/372

*Primary Examiner*—Lee Cohen
*Attorney, Agent, or Firm*—Morrison & Foerster LLP

[57] ABSTRACT

A planar electrode which enables multi-point simultaneous stimulation and recording of nerve cells over a long time is provided, which also has excellent response property. An ITO film is evaporated on the whole surface of an insulating substrate of the hard glass, and the ITO film is etched so that the central portion of each electrode is located on each intersection of 8×8 lattices, the center-to-center distances of nearest electrodes of each electrode are equal, and a lead wire is stretched radially. Then, for an insulating layer, negative photo-sensitive polyimide is spin-coated, and an insulating layer pattern is exposure-formed so that a 50 $\mu$ms square hole is produced at the center of each electrode. Furthermore, to the exposed portion of each electrode (that is, the inside of the 50 $\mu$ms square), Ni is evaporated in a film thickness of 500 nm, which is followed by evaporating gold (50 nm) and platinum black (about 1 $\mu$m). The contact with the external circuit of the section near the end opposite to the electrode of the lead wire was coated with gold and nickel.

8 Claims, 5 Drawing Sheets

PLANAR ELECTRODE

This application is a continuation of U.S. Ser. No. 08/481,149, filed Jun. 7, 1995, now U.S. Pat. No. 5,810,725, which is a continuation-in-part of U.S. Ser. No. 08/114,634, filed Sep. 2, 1993, now abandoned.

FIELD OF THE INVENTION

This invention relates to a planar electrode which is used in the field of neurophysiology for electric measurement of biological activities, in particular, of the electric activities of nerve cells. This planar electrode comprises a large number of electrodes.

BACKGROUND OF THE INVENTION

Recently, medical investigations on nerve cells and investigations of the possibility of using nerve cells as electric elements have been actively pursued. When nerve cells are active, action potential is generated. The action potential is generated by the change of ion concentration inside and outside the cell membrane which is accompanied by the change of ion permeability in nerve cells. Measuring this potential change accompanied by the ion concentration change (that is, the ion current) near the nerve cells with electrodes enables the detection and investigation of nerve activities.

Conventionally, in order to measure the electrical activities of nerve cells, it is common practice to use a recording electrode comprising glass or other electrodes and a stimulating electrode comprising metal or other electrodes, insert each of them in or between cells, and measure the electrical activities of nerve cells with the recording electrode when a stimulating current (or voltage) is applied from the stimulating electrode.

In addition to this, there are many modified methods such as the so-called patch clamp method, in which a cell body is pierced with a capillary glass suction electrode, the inside of the cell body is refluxed with the liquid in the glass suction electrode, and electrical signals are emitted from this glass suction electrode to observe electric characteristics of the cell membrane.

Furthermore, a method of recording electrical activities of nerve cells is proposed separately from the inventors of this invention, which is accomplished by forming electrodes made of a conductive material such as ITO (indium tin oxide) on the surface of an insulating substrate with a diameter of 15 to 20 $\mu$m, enabling culture of nerve cells on the electrodes, and applying electric stimulation to cells without piercing the cells with electrodes.

As an improvement of this method, the inventors of this invention also propose separately to form electrodes with a diameter of 20 to 200 $\mu$m, so that an electric potential difference arising between the electrodes becomes smaller when constant current stimulation is applied to nerve cells. As a result, ITO is less likely to be destroyed, thereby enabling even more long-term observation.

In the above-mentioned conventional technique and its modified methods, electrodes such as glass electrodes, which have to be larger than the cells themselves, must be urged. As a result, primarily due to restrictions of space and operating accuracy, multi-point simultaneous measurements in which two or more recording electrodes are inserted simultaneously in one sample to record electrical activities of the nerve cells are extremely difficult.

In order to investigate the operation of the whole nerve circuit network, it is necessary to record many nerve cell activities simultaneously, and as the number of measuring points increases, the degree of difficulty increases, creating the problem that it is difficult to observe throughout a large number of cells.

In addition, because glass, metal, or other electrodes must be pierced into or between cells, there is another problem that the damage to the cell is serious and measurement over a long time such as extending for more than a few hours is difficult to carry out.

On the other hand, signal transmission throughout a large number of cells can be observed by using an insulating substrate formed thereon with circular (or square) electrodes made of a conductive material such as ITO with a diameter (or a side) of 15 to 20 $\mu$m. However, due to the small area of the electrodes ranging from 177 $\mu$m$^2$ to 400 $\mu$m$^2$, the electrode resistance at the interface of culture solution becomes several M$\Omega$. Since the stimulation is generally provided as constant electric current, an extremely large potential difference arises between the electrodes when the electric resistance is large. Thus, ITO is destroyed when a long-term electric stimulation is provided under such large voltage, creating the problem that it is difficult to carry out observations over a long time.

In addition, when the electrode area ranges from 400 $\mu$m$^2$ to 40000 $\mu$m$^2$, the electrode resistance at the interface of culture solution is reduced, and a potential difference arising between the electrodes becomes comparatively small. Even if the stimulating electric current was provided over a long time, destruction of ITO was not observed by a microscope. However, when a stimulating current was applied at a certain electrode and a potential change accompanied by the stimulation was recorded at other electrodes, a great change was observed in the recording waveform before and after long stimulation. In other words, the effects of the applied stimulating current on the recording waveform (that is, artifacts) were greater after long stimulation than before long stimulation. The reason for this waveform change is considered to be caused by polarization on the electrode surface. In the worst case, the electrical activities of the nerve cells were hidden by the artifacts and measurement was disabled. Furthermore, even if the artifacts are not so great, there was another problem that it becomes difficult to compare strength of nerve activities before and after long stimulation.

SUMMARY OF THE INVENTION

Accordingly, a feature of the invention is to provide a planar electrode which solves these conventional problems and enables easy multi-point simultaneous stimulation and measurement of nerve cells as well as signal transmission and observation throughout many cells for more than just a few hours. The planar electrode of the invention also enables suppressing generation of artifacts which is accompanied by applied stimulating electric current, and comparison of potential recording waveforms before and after long stimulation.

In order to accomplish these and other objects and advantages, a planar electrode of this invention has a multiplicity of electrodes for measurement of electric activities of nerve cells in an organism, and comprises an insulating substrate, a multiplicity of electrodes disposed thereon, a wiring section in which lead wires are installed from the electrodes, and an insulating layer covering the lead wires, and the electrodes each has an area from 4×10$^2$ $\mu$m$^2$ to 4×10$^4$ $\mu$m$^2$, wherein impedance is in the range of 1 $\Omega$ to 100 k$\Omega$ when the electrode section is covered with an electrolytic solution and an alternating voltage of 1 kHz, 50 mV is provided to an optional portion between the electrolytic solution and the lead wires.

It is preferable in this invention that the lead wire comprises an indium tin oxide alloy. Accordingly, continuity can be established with reliability even if the wire is thin. In addition, when an indium tin oxide alloy is used for the lead wire, the lead wire becomes transparent with a slightly yellowish color. This feature is preferable for attaining good visibility of nerve cells and also for operations in experiments.

Furthermore, it is preferable in this invention that the electrode is comprised of an indium tin oxide alloy, covered thereon with at least one metal selected from the group consisting of Ag, Al, Bi, Au, Cu, Cr, Co, and Ni, and coated thereon with a metal containing platinum. This structure enables establishment of reliable continuity with low impedance. In addition, even if the electrode comes into contact with an electrolyte, no alternation such as oxidation occurs.

In addition, it is preferable in this invention that the lead wire drawer section is comprised of an indium tin oxide alloy, covered thereon with at least one metal selected from the group consisting of Ag, Al, Bi, Au, Cu, Cr, Co, and Ni. This structure can attain strong oxidation resistance and is convenient to take out electric signals from electrodes.

Also, when the shortest electrode-to-electrode distance between adjacent electrodes in the multiplicity of electrodes is substantially equal in this invention, it is convenient to measure electric stimulation signals of nerve cells etc. Here, the electrode-to-electrode distance indicates the distance of the closest parts in the electrodes.

When the electrode-to-electrode distance is in the range of 10 $\mu$m to 1000 $\mu$m in this invention, it is similarly convenient to measure electric stimulation signals of nerve cells etc.

It is preferable in this invention that the lead wires are installed substantially radially from the electrodes to reduce the capacitance between the lead wires.

Furthermore, it is preferable in this invention that a solution holding section for holding a cell culture liquid medium is present in a position surrounding a group of multielectrodes.

Thus, measurements can be performed while culturing cells for a long period of time.

In addition, it is preferable in this invention that the insulating layer covering the lead wires has holes above each electrode and is provided approximately on the entire surface of the insulating substrate except in the vicinity of contact points between an external circuit and the lead wires. In this way, even if an electrolytic solution or a culture liquid medium is dropped, the lead wires are not directly touched and remain electrically stable. In particular, the insulating layer comprising a polyimide resin or an acrylic resin is chemically and thermally stable.

Also, when centers of the multiplicity of electrodes are located at each intersection of an 8×8 lattice in this invention, it is practically sufficient to measure nerve cells in an organism.

The electrolytic solution comprising a NaCl aqueous solution of 1.4 vol. % is close to a cell culture liquid medium. Since electric conductivity is close to a cell culture liquid medium actually used for measurments of nerve cells in an organism, it is suitable for measuring impedance when an alternating current is passed to an optional section between the electrolytic solution and the lead wires. This is because measurements can be conducted under the conditions which are close to an environment to be used.

In addition, it is practical that impedance is in the range of 1 k$\Omega$ to 60 k$\Omega$ when an alternating voltage of 1 kHz, 50 mV is provided to an optional portion between the electrolytic; solution and the lead wires.

The planar electrode of the invention enables detection of the transmission of signals between adjoining cell bodies in providing signals to nerve cells cultured on the planar electrode of the invention and measuring the signal between cells at the same time. This is because one cell body is arranged on the electrode, and it can be arranged with a high degree of probability that the cell body mediating the cell protrusions (e.g., dendrites and axons on nerve cells) will be located on adjoining electrodes by adjusting the shortest electrode-to-electrode distance to be nearly equal to the length of a nerve cell to be measured (that is, cell body, dendrites, axon) and equally spacing the electrodes.

Furthermore, arranging the lead wires extending from the electrodes substantially radially reduces the capacitive component (capacitance) between lead wires from the capacitance when they are arranged in parallel. The collapse of pulse signal waveform, electrical signals, is also reduced, and the time constant of the circuit becomes small, improving the response to quick pulse signals and therefore improving the follow-up to the component with fast nerve cell activities.

In addition, adjusting the electrode area in the range from $4 \times 10^2$ to $4 \times 10^4$ $\mu m^2$ enables application of electric stimulation to a cell over a long time extending for more than a few hours as well as measurement of electric activities of the cell.

Determining the impedance to achieve the desired range of 1 $\Omega$ to 100 k$\Omega$ substantially prevents polarization on the stimulating electrode surface of the nerve cell from occurring when a stimulating current is applied for a long time to nerve cells at a certain electrode and electrical activities (potential change) of the nerve cells are recorded corresponding to the stimulating current at other electrodes, thereby minimizing the effects (that is, artifacts) of stimulating current on potential recording waveform. In particular, because even after a stimulating current is applied over a long time, artifacts are small and the mode is free from change, so electrical activities of nerve cells before and after long stimulation can be compared.

In addition, in the planar electrode of the invention, bringing the shortest electrode-to-electrode distance to the desirable condition of 10 to 1000 $\mu$m results in a high possibility of locating the cell bodies on adjoining electrodes and connecting them via their axons, since nerve cells generally have axons with a length within this range under culture conditions, achieving an electrode-to-electrode distance convenient for measurement of nerve cells.

In the planar electrode of the invention, the desirable form of the insulating layer, in which the insulating layers covering lead wires have holes over each electrode and are installed on nearly the whole surface of the insulating substrate except the vicinity of the section where the lead wire comes in contact with the external circuit, allows easy formation of the required insulating layer by applying the insulating material comprising photo-sensitive resin to nearly the whole surface and removing the insulating layer on each electrode by a photoetching method and opening holes to expose electrodes, thereby achieving easy production and minimizing the probability of insulation failure, which is very desirable. This process is superior to optionally forming insulating layers merely on lead wires.

Furthermore, in the planar electrode of the invention, locating the center of a multiplicity of electrodes at each intersection of 8×8 lattices secures the maximum number of electrodes which enables installation of lead wires substantially radially from the electrodes of the invention, which is very desirable.

DETAILED DESCRIPTION OF THE INVENTION

Figure 1:
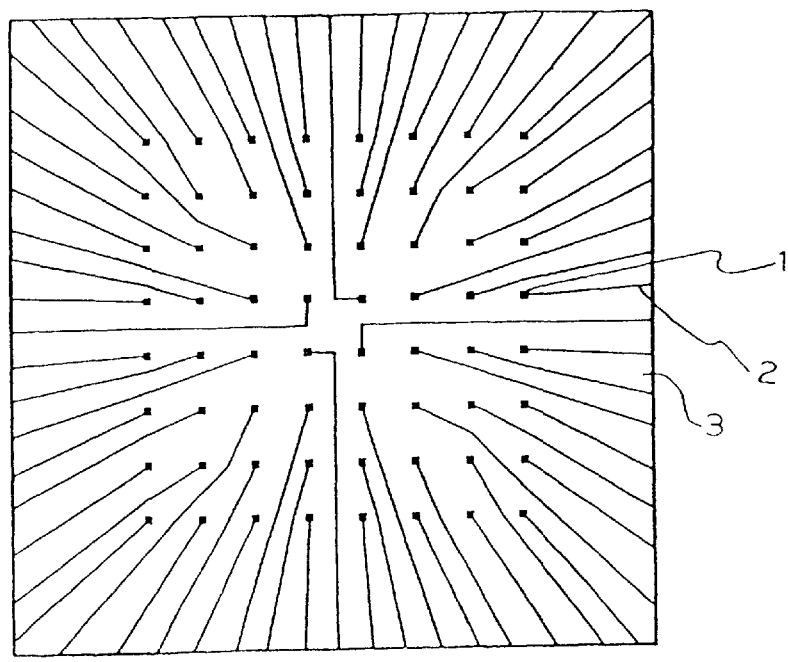
FIG. 1 is a plan view showing a pattern in the center of a wire section prior to the application of an insulating layer on the planar electrode of the invention with electrodes and lead wires formed on an insulating substrate in an embodiment of this invention.

As the insulating substrate material used for the invention, a transparent substrate is desirable because microscopic observation is required throughout the experiment. Examples include glasses such as quartz glass, lead glass or borosilicate glass, or inorganic substances such as quartz, or organic substance with transparency such as polymethyl metacrylate or its copolymers, polystyrene, polyvinyl chloride, polyester, polypropylene, urea resin, and melamine resin. Considering mechanical strength in combination with transparency, though, inorganic substances are desirable.

As the electrode materials used for the invention, examples include indium tin oxide (ITO), tin oxide, Cr, Au, Cu, Ni and Al. ITO is particularly desirable for its good conductivity.

The same materials can be applied to lead wires, and ITO is again desirable for the similar reason mentioned above. In particular, by using the same material for the lead wire section and the electrode section and manufacturing them in a lump, the manufacturing process can be simplified and the connection between the lead wire section and the electrode section is even more assured.

It is not a particular restriction of the invention, but in general the thickness of the electrodes and lead wires should be about 50–500 nm and, in general, these materials are evaporated on the insulating substrate and formed in a desired pattern by etching using a photoresist.

As the insulating layer material used to insulate the lead wires used for the invention, examples include polyimide (PI) resin, epoxy resin, acrylic resin, polyester resin, polyamide resin, and other transparent resins.

These types of resin are applied on lead wires by conventional techniques to form an insulating layer. When the insulating material is a photosensitive resin which has photochemical polymerization properties, etc., it is desirable because patterns can be formed to provide holes on the insulating layer portion on the electrodes to expose the electrodes as described above.

In particular, when insulating material is PI or acrylic resin and the cell to be cultured is a nerve cell, satisfactory growth takes place and therefore, it is very desirable. In addition, among types of PI, negative photosensitive polyimide (NPI) is most desirable because holes can be formed on the electrodes using a photo etching process after the negative photosensitive polyimide is applied over nearly the whole surface, in a manner similar to that in forming patterns of the wiring section.

The thickness of the insulating layer may be such that can impart insulating capability. This is not particularly limiting but in general, a thickness of 0.1–10 μm, specifically, one of 1–5 μm is desirable.

The planar electrode of the invention was used to directly culture cells and to measure and record electrical activities of the cells. Depending on culture conditions or the type of cells, the size of cell body or the length of cell protrusion such as dendrites or axons may vary but 10–1000 μm is desirable for the electrode-to-electrode distance of the closest planar electrodes. When the electrode-to-electrode distance is less than 10 μm, the electrodes are so close to one another that the probability for the cell bodies to adjoin via cell protrusions decreases. Furthermore, wiring of lead wires become difficult. When the electrode-to-electrode distance exceeds 1000 μm, lead wires can be easily wired but as it is rare for the cell protrusions to elongate as far as about 1000 μm under culture conditions, the probability of the cell bodys bonded via protrusions and synapses located at the ends of the protrusions to be located on the electrode decreases. Even under general culture conditions, about 200–300 μm is desirable for the electrode-to-electrode distance because the length of cell protrusions of a cultured cell is about 200–300 μm on average for central nervous system cells of mammals.

With respect to the electrode area, in order to avoid electrode breakage which occurs when electric stimulation is applied to the nerve cells over a long period of time and also to avoid excessive polarization, it is necessary to reduce the impedance at the interface with the culture medium, requiring a size exceeding a certain level.

Furthermore, when the impedance at the interface of the electrode and the culture medium becomes smaller, thermal noise arising at this part is reduced. On the other hand, a potential change accompanied by the activities of the nerve cells which is detected by the electrode is usually measured via an amplification circuit disposed outside. It is common to use an amplification circuit having an extremely high input impedance (for example, several hundreds MΩ) the value of the measured potential change is hardly different, even if a slight change of impedance (for example, change from several MΩ to several kΩ) may be observed at the interface of the electrode and the culture medium. Therefore, the signal to noise (S/IN) ratio of the measurement improves as a whole, so that it is also advantageous from this aspect.

However, since the impedance at the interface of the electrode and the culture medium is reduced, if the electrode area is enlarged too much, a multiplicity of nerve cells must be placed on one electorde. In this case, the potential change to be measured indicates the average activities of the multiplicity of the nerve cells, so that it is extremely difficult to analyze the activities of each nerve cell. Consequently, the electrode area must be determined carefully according to the object of the experiment.

In general, by taking the length of protrusion elongation of the nerve cells under the above-mentioned culture conditions and other factors into consideration, it is desirable that the electrode area ranges from $4 \times 100 \ \mu m^2$ to $4 \times 10000 \ \mu m^2$, and more preferably, from $1 \times 1000 \ \mu m^2$ to $1 \times 10000 \ \mu m^2$.

In order to reduce the impedance between the electrode and an optional point on the lead wire to be 100 k$\Omega$ or less when 1.4 vol. % NaCl is filled on the electrode and an alternating voltage of 1 kHz, 50 mV is provided, the ITO top surface is coated with metal. At least one of the coating materials selected from the group consisting of Ag, Al, Bi, Au, Cu, Cr, Co, and Ni can be used here, but with low toxicity to nerve cells taken into account, the use of Au is desirable. The coating thickness is not, in particular, limited, but is from 50 to 500 nm and, in general, these materials are evaporated on the insulating substrate and are formed into desired patterns by etching using a photoresist. When platinum black is coated, corrosion-resistant property is improved, and at the same time, the impedance is lowered, thereby also improving the conductivity.

In addition, according to a preferred embodiment of the invention described previously, holes in the insulating layer of the planar electrode are formed to expose electrodes not only to give electrical stimulation to the cell body cultured on the planar electrode but also to detect electrical activities from adjoining cell bodies which are located at the central portion of the electrode.

Arranging lead wires stretched from the electrode nearly radially eliminates the capacitance between lead wires, reduces the time constant, and improves the measuring accuracy.

The configuration in which the electrode center portion of the planar electrode of the invention is located concentrically or at each intersection of lattices of 8×8 or smaller enables the lead wire to be radially installed, and from the viewpoint of particularly forming as many electrodes as possible and providing and recording multi-point stimulation simultaneously, it is desirable to install electrodes at each intersection of the 8×8 lattices.

Now referring the following specific embodiments, the planar electrode of the invention will be described in further detail.

(Embodiment 1)

Figure 2:
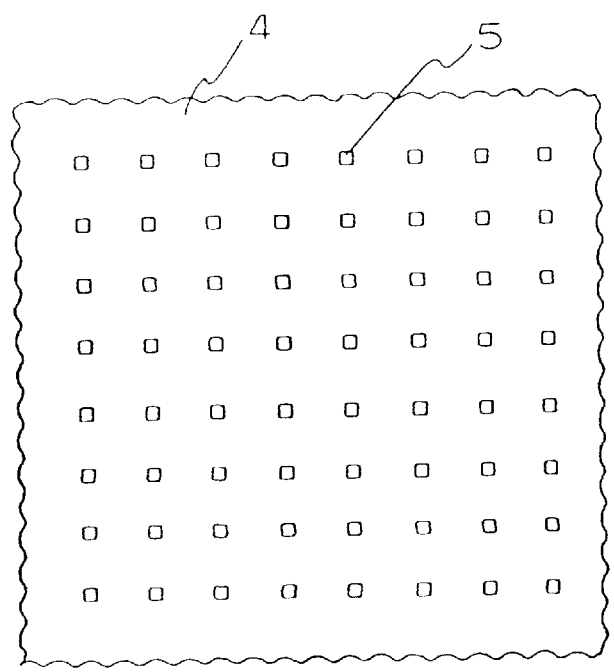
FIG. 2 is a partially notched view of the plan view of FIG. 1 having the insulating layer of an embodiment of the invention applied to a planar electrode.
Figure 3:
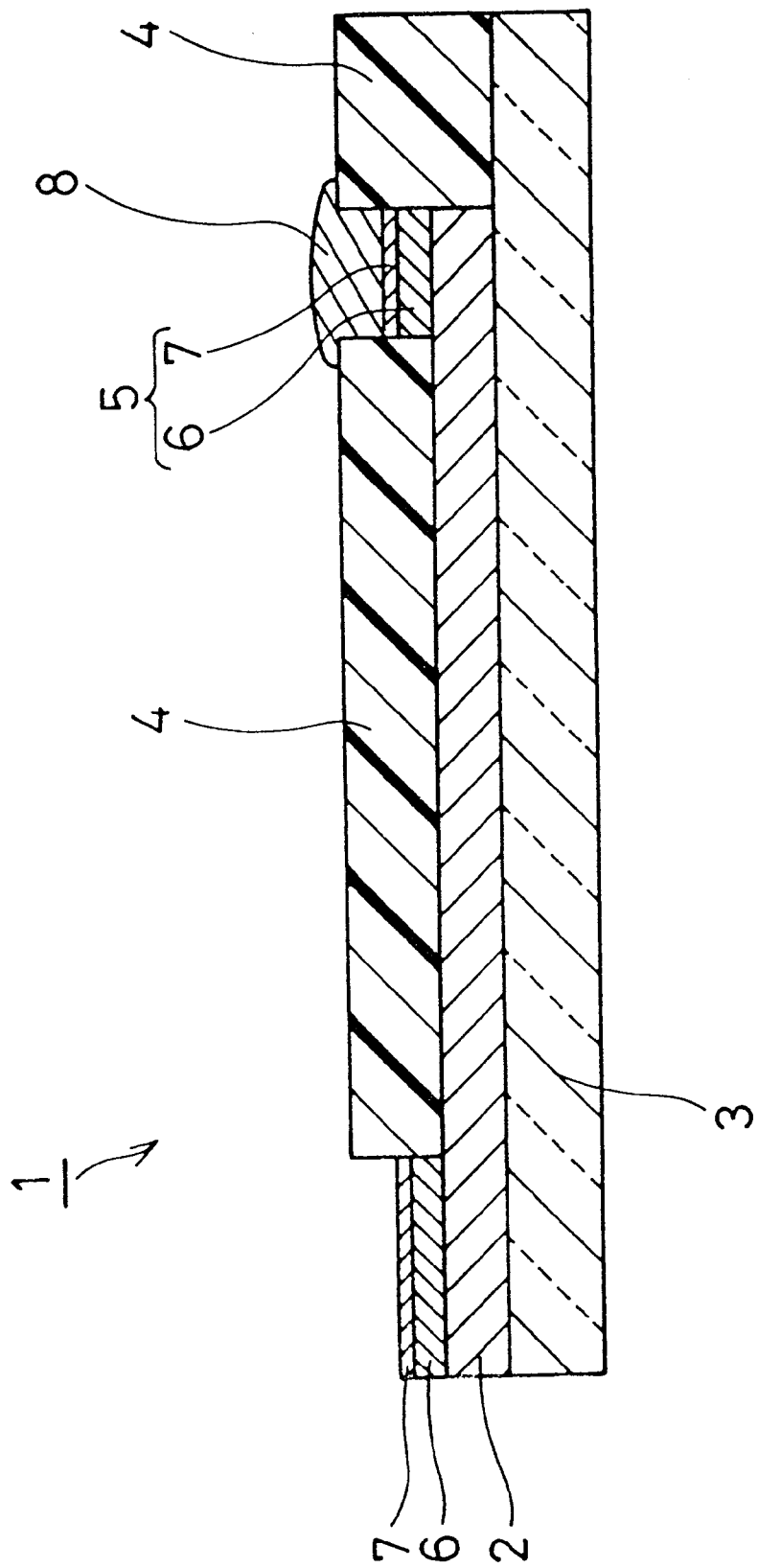
FIG. 3 is a fragmentary cross sectional view of an embodiment of a planar electrode of the invention.

FIG. 1 is a plan view showing a pattern in the center of a wire section prior to the application of an insulating layer on the planar electrode of the invention with electrodes 1 and lead wires 2 formed on an insulating substrate 3. FIG. 2 is a partially notched view of the plan view having the insulating layer applied to a member shown in FIG. 1. FIG. 3 is a fragmentary cross sectional view showing a planar electrode of this invention. In FIG. 1, reference numeral 1 represents an electrode for detection of electric activities of a cell body; 2 represents a lead wire to be connected to the electrode 1; and 3 represents an insulating substrate such as glass. In FIG. 2, 4 represents an insulating layer comprising a polyimide resin etc., and 5 represents a hole opened in the insulating layer 4 for forming electrodes. Next in FIG. 3, 1 represents a planar electrode; 2 represents an ITO (indium tin oxide alloy) layer which was formed on top of an insulating substrate 3 comprising glass etc.; 4 represents an insulating layer such as a polyimide resin; 6 represents a layer formed on the surface of the ITO layer 2, for example, a Ni layer; and 7 represents an Au layer formed thereon. 5 represents a foundation electrode section comprising the Ni layer 6 and the Au layer 7 disposed thereon. 8 represents a surface layer electrode section comprising, for example, platinum black formed on the surface of the foundation electrode section 5.

It will be explained in the following by referring to these figures.

First, fabrication of a planar electrode wiring section is described. As the insulating substrate 3 of the planar electrode in FIGS. 1 and 3, 50×50×1 mm hard glass ("IWAKI CODE 7740 GLASS"—Iwaki Glass Co., Ltd. or "CORNING 7059") was used; this is a transparent insulating material with high mechanical strength. For the material of electrode 1 and lead wire 2, ITO was used, and on the whole surface of the insulating substrate 3 of the hard glass, ITO was evaporated to form a layer about 1500 angstrom (150 nm) thick, which was followed by rinsing.

Then, the substrate was exposed to light through a photoresist so that the central portion of each electrode 1 was located on each intersection of 8×8 lattices (position 5 as shown in FIG. 2), the center-to-center distances of nearest electrodes of each electrode were equal, and lead wire 2 formed the pattern of electrode I and lead wire 2 in which lead wire 2 was stretched radially. It was then etched with ITO in a solution which was made up using demineralized water, hydrochloric acid, and nitric acid in a volume ratio of 50:50:1, and the photoresist was removed. The wiring portion with electrode 1 being 60 $\mu$ms square, lead wire 2 being 30 $\mu$m wide, and a center-to-center distance of electrodes of 300 $\mu$m (that is, the electrode-to-electrode distance is 240 $\mu$m) was thus formed.

Then, for insulating layer 4, negative photo-sensitive polyimide (hereinafter called "NIP") was spin-coated so that a film 1.4 $\mu$m thick was formed after drying, and an insulating layer pattern was exposure-formed so that a 50 $\mu$ms square hole 5 was produced at the center of each electrode of the wiring section as shown in FIG. 2. As shown in FIG. 3, to the exposed portion of each electrode (that is, the inside of the 50 $\mu$ms square), Ni 6 was evaporated to form a film of 500 nm thick, and on top of this Ni layer 6, gold 7 was evaporated to form a film of 50 nm thick, thereby forming the foundation electrode section 5. Contact points between the lead wires 2 and an external circuit of the section near the end opposite to the electrode were also coated by evaporating Ni 6 in a film thickness of 500 nm and gold 7 on top of the Ni layer 6 in a film thickness of 50 nm to improve durability. The surface layer electrode section 8 comprising a platinum black layer was formed on the surface of the foundation electrode section 5 in the following method.

For the convenience of performing the coating process, a polystyrene cylinder having an inner diameter 22 mm, an outer diameter 26 mm, and a height 8 mm was adhered in the following steps. This polystyrene cylinder can be sterilized and used as a culture container for culturing nerve cells on a planar electrode.

Figure 8:
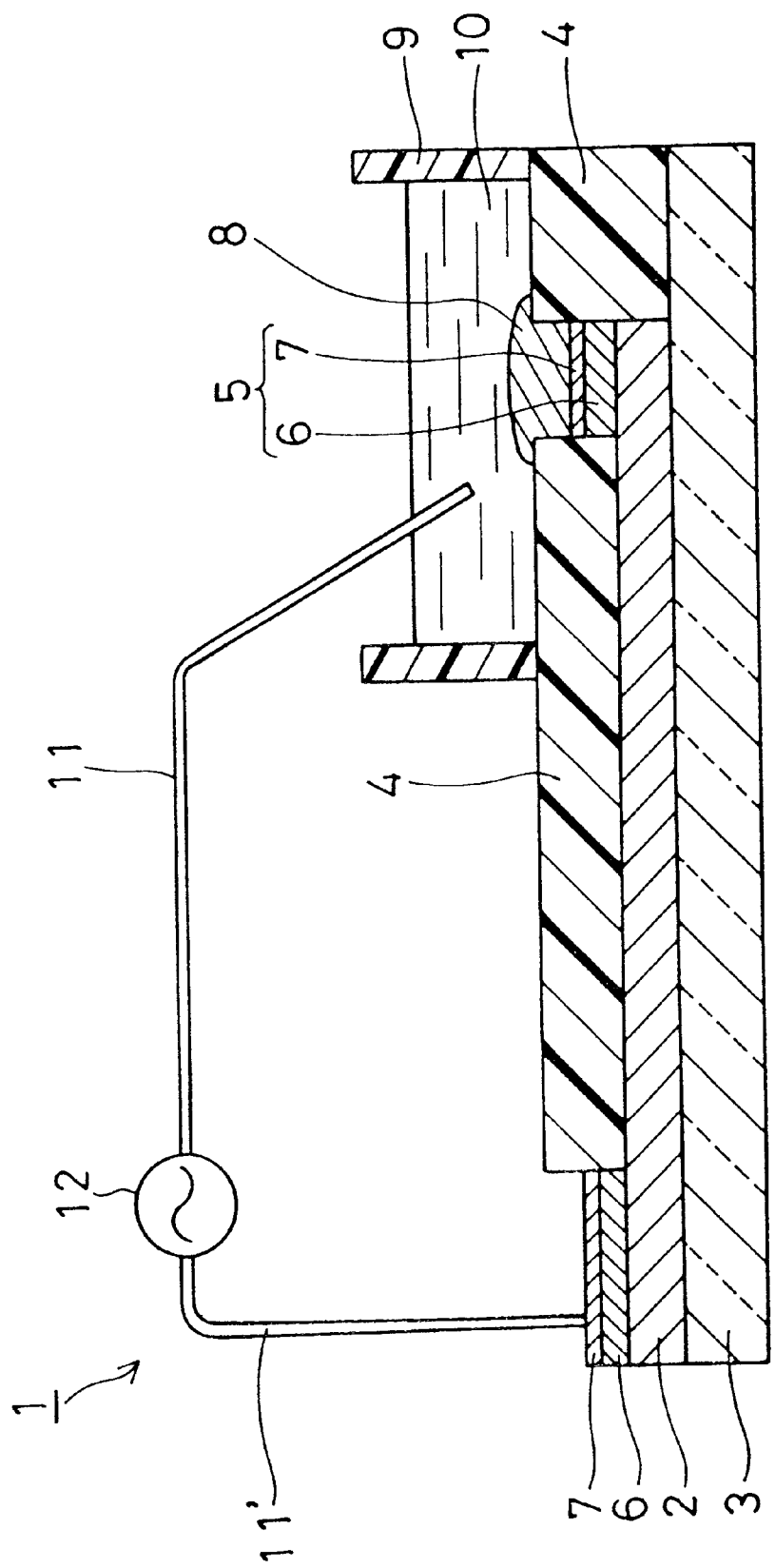
FIG. 8 is a fragmentary cross sectional view showing a method of measuring impedance in an embodiment of the planar electrode of this invention.

(a) On the bottom face of a polystyrene cylinder (inner diameter 22 mm, outer diameter 26 mm, height 8 mm)

shown as 9 in FIG. 8, a sufficient amount of an one-liquid silicon adhesive (DOW CORNING CO., LTD. 891 or SHIN-ETSU CHEMICAL CO., LTD. KE-42RTV) was applied.

(b) The center of a glass substrate in the planar electrode and the center of the polystyrene cylinder 9 were carefully matched and then adhered in this condition.

(c) By leaving in an environment in which dusts hardly enter for 24 hours, the adhesive was solidified.

The microelectrode surface was coated with platinum black in the following steps.

(a) The above-mentioned polystyrene cylinder 9 was filled with 1 ml of solution comprising 1 vol. % chloroplatinic acid, 0.0025 vol. % HCl, and 0.01 vol. % lead acetate (hereinafter abbreviated as a platinum solution).

(b) A platinum wire having a diameter of 0.2 mm was dipped in the platinum solution up to a length of about 1 cm.

(c) By using the above-mentioned platinum wire as the positive electrode and one of microelectrodes selected optionally as the negative electrode, DC voltage was applied for 1 minute to pass electric current with current density of 20 mA/cm$^2$ between the two electrodes. According to this operation, platinum black (3 in FIG. 8) of about 1 $\mu$m thick was deposited on the surface of the microelectrode serving as the negative electrode.

(d) The operation of Step (c) was conducted for each microelectrode, so that this operation was repeated for a total of 64 times.

(e) Alternatively, by shorting contact points from the microelectrodes via the lead wires with an external circuit and by using them altogether as the negative electrode, platinum black can be deposited on the surface of a multiplicity of microelectrodes simultaneouly. At this time, however, the DC voltage to be applied is adjusted to maintain the current density of 20 mA/cm$^2$.

The impedance was measured in the following steps.

(a) The above-mentioned polystyrene cylinder 9 was filled with 1 ml of 1.4 vol. % NaCl solution 10.

(b) A platinum wire 11 having a diameter of 0.2 mm was dipped in the 1.4 vol. % NaCl solution 10 up to a length of about 1 cm.

(c) By using the above-mentioned platinum wire 11 as one end and by selecting the other end optionally from contact points 6, 7 from the microelectrodes via the lead wires 2 with an external circuit, AC voltage of 1 KHz, 50 mV was applied between the two ends, and impedance was measured. The measurement was conducted by using a LCR meter (YHP 4274A). As a result of the measurements, an average value of impedance was 10 k$\Omega$ when platinum black was present. On the other hand, the average value of impedance was 500 k$\Omega$ when platinum black was not present. Accordingly, it was confirmed that the coating of platinum black greatly improved conductivity.

In this embodiment, ITO was used for electrode 1 and lead wire 2, NPI for the insulating layer, and gold for the electrode surface coating material, but it has already been stated that the material used shall not be limited to these.

The process of producing the planar electrode of the invention is not limited to the method described in this embodiment.

(Embodiment 2)

Next, the culture of nerve cells on the planar electrode is described.

On the planar electrode formed in Embodiment 1, cerebral visual cortex cells of rats were cultured as the nerve cells.

Now, the culture method will be discussed in detail.

(a) Brains of fetuses of SD rats at 16–18 days of pregnancy were removed and immersed in iced Hanks' Balanced Salt Solution (hereinafter called "HBSS").

(b) From the brains in the iced HBSS, visual cortices were cut out and transferred to Eagle's minimum essential medium (hereinafter called "MEM") liquid.

(c) In the MEM liquid, the visual cortices were cut into as small pieces as possible, 0.2 mm square at maximum.

(d) The visual cortices cut into small pieces were placed in centrifugal tubes (test tubes for centrifugal separation), and after washing with HBSS free from calcium and magnesium (hereinafter called "CMF-HBSS") three times, they were dispersed in a suitable volume of the same liquid.

(e) In the centrifugal tubes of Step (d), a CMF-HBSS solution of trypsin (0.25 wt %) was added to double the total volume. With gentle stirring, enzymatic processes were allowed to take place while the solution was incubated at 37° C. for 15 to 20 minutes.

(f) DMEM/F-12 mixture medium in which Dulbecco modified Eagle's medium (DMEM) and HamF-12 medium were mixed in a volume ratio of 1:1 and provided with 10 vol. % of fetal cow serum (FCS) was added to the centrifugal tube subjected to Step (e) to further double the total volume. With a Pasteur pipette with a reduced diameter produced by fire-polishing the tip end with a burner, gently repeating pipetting (about 20 times at maximum), the cells were unravelled.

(g) Centrifugation was carried out for about 5 minutes at 9806.65 m/sec$^2$ (that is, 1000 g). Upon completion of centrifugation, the supernatant was discarded and the precipitate was suspended in DMEM/F-12 mixture medium containing FCS 5 vol. %.

(h) Step (g) was repeated two more times (a total of 3 times).

(i) The precipitate finally obtained was suspended in the DMEM/F-12 mixture medium containing 5 vol. % FCS and using an erythrocytometer, the cell concentration in the suspension liquid was measured. Using the similar medium, the cell concentration was adjusted to be 2×10$^6$ to 4×10$^6$ cells/ml.

(j) In a well for cell culture formed by affixing a polystyrene cylinder (inner diameter 22 mm, outer diameter 26 mm, height 8 mm) to the planar electrode with the planar electrode center aligned with the polystyrene cylinder center, 500 $\mu$L of the DMEM/F-12 mixture medium containing 5 vol. % FCS was added in advance and heated in a CO$_2$ incubator (air content: 95 vol %; CO$_2$ content: 5 vol %; relative humidity: 97%; Temperature: 37° C.).

(k) In the well of Step (j), 100 $\mu$L of the suspension liquid with the cell concentration adjusted was gently added and again let stand in the CO$_2$ incubator.

(l) Three days after the performance of Step (k), one half the medium was replaced with a new one. For the replaced medium, the DMEM/F-12 mixture medium not containing FCS was used.

(m) Thereafter, half of the medium was replaced in the similar manner every 4 to 5 days.

Over the series of these operations, nerve cells of cerebral visual cortices of rats were cultured on the planar electrodes.

The cells grew successfully even on the insulating layer (NPI) and even on the electrodes with platinum black deposited on them. Consequently, the use of the electrodes suitably located for the stimulation electrodes or recording electrodes enabled the simultaneous multi-point measurement of the electrical activities of nerve cells.

Figure 4:
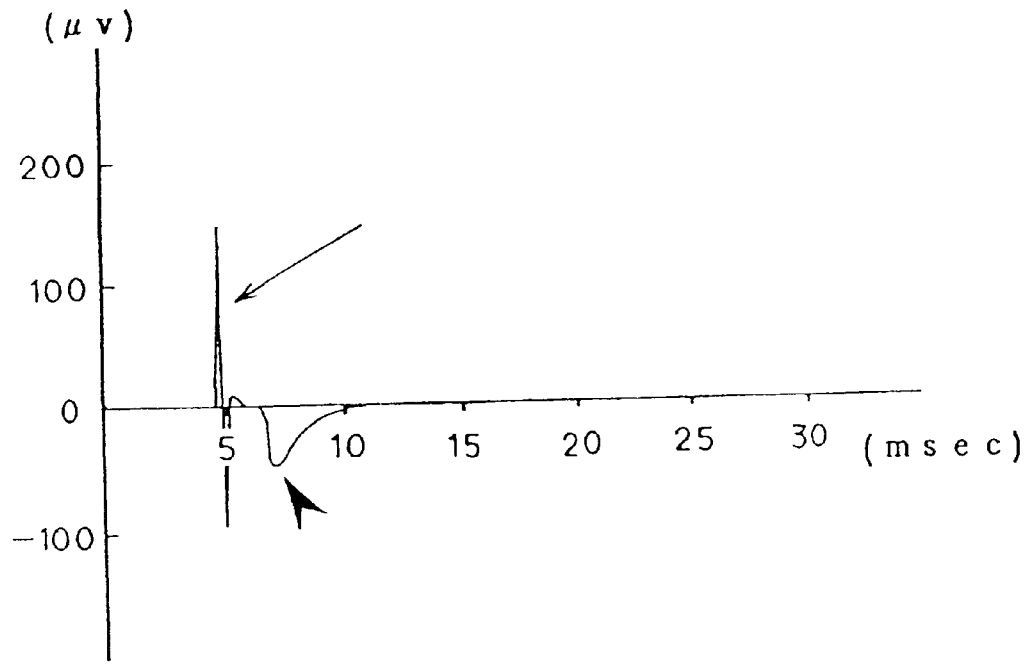
FIG. 4 shows a changing potential waveform recorded with other suitable electrodes before applying stimulating current over a long time using suitable electrodes in an embodiment of the planar electrode of the invention.
Figure 5:
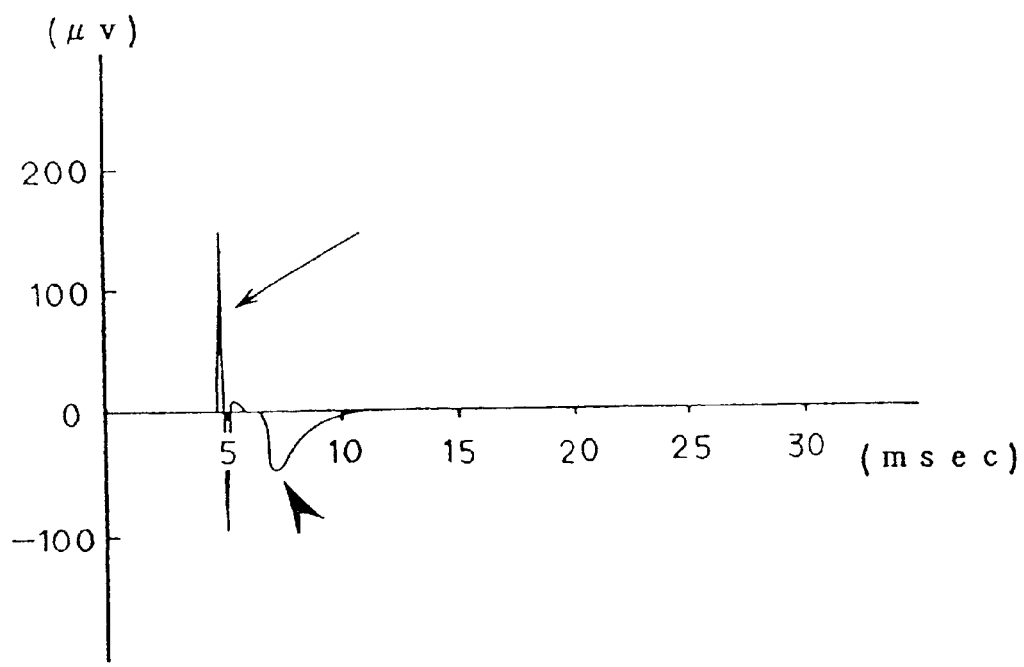
FIG. 5 shows the changing potential waveform recorded with other suitable electrodes after applying stimulating current over a long time using suitable electrodes in an embodiment of the planar electrode of the invention.

FIGS. 4 and 5 show examples of electrical responses (potential changes) of nerve cells at the electrodes located at suitable places recorded before and after constant current stimulation of 100 $\mu$A was provided over one week at a frequency of 1 Hz via the electrodes suitably located in the planar electrode of the invention. FIG. 4 shows the electrical responses of the nerve cells before stimulation, while FIG. 5 shows the electrical responses of the nerve cells after stimulation.

Figure 6:
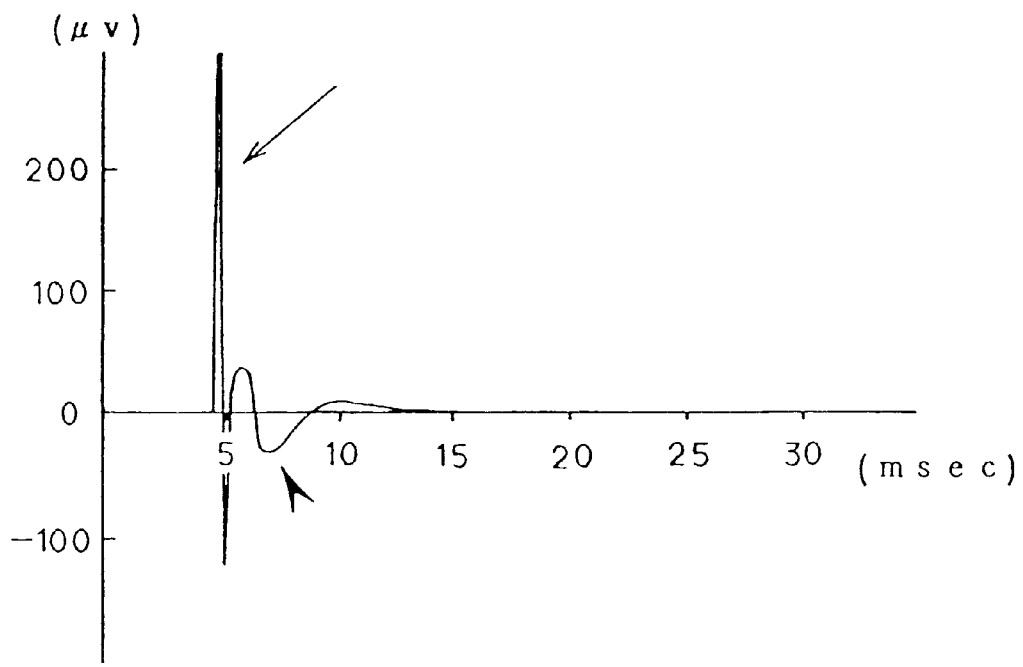
FIG. 6 shows the changing potential waveform recorded with other suitable electrodes before applying stimulating current over a long time with suitable electrodes, using a planar electrode which differs from the planar electrode of the invention only in that the electrode surface is not coated with Ni, Au, and platinum black.
Figure 7:
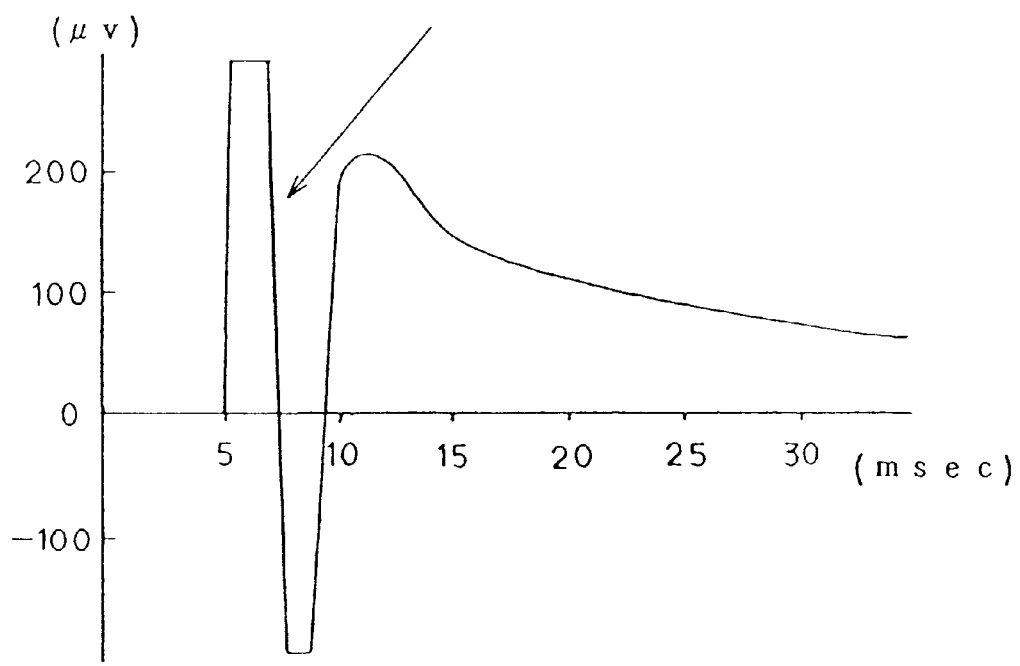
FIG. 7 shows another kind of the changing potential waveform recorded with electrode after applying stimulating current over a long time with suitable electrodes, using a planar electrode which differs from the planar electrode of the invention only in that the electrode surface is not coated with Ni, Au, and platinum black.

In addition, FIGS. 6 and 7 show examples of electrical responses of nerve cells recorded before and after long-term stimulation was applied under the same conditions as above, using a planar electrode whose surface is not coated with Ni, Au, and platinum black. FIG. 6 shows the records of electrical response of nerve cells before stimulation, while FIG. 7 shows the records of electrical response of nerve cells after stimulation.

In FIGS. 4 through 7, the arrow marks show the artifacts generated as a result of application of stimulation current and the arrow head shows a potential change generated by electrical activities of nerve cells.

As is clear from FIG. 6, when the planar electrode whose surface is not coated with Ni, Au, and platinum black is used, generation of artifacts is great, while when the planar electrode of one embodiment of the invention shown in FIG. 4 is used, generation of artifacts is suppressed.

As is clear from FIG. 7, when the planar electrode surface is not coated with Ni, Au, and platinum black, generation of artifacts is greater after than before stimulation; the electrical activities of the nerve cells are hidden by the artifacts and measurement is disabled. In contrast, when the planar electrode of one embodiment of the invention as shown in FIG. 5 is used, same as in the case shown in FIG. 4, generation of artifacts is suppressed and the electrical activities of the nerve cells are successfully recorded.

There are many other methods than those described above for the culture of nerve cells on the planar electrode of the invention.

The invention may be embodied in other specific forms without departing from the spirit or essential characteristics thereof. The disclosed embodiments are to be considered in all respects as illustrative and not restrictive, the scope of the invention being indicated by the appended claims rather than by the foregoing description and all changes which come within the meaning and range of equivalency of the claims are intended to be embraced therein.

What is claimed is:

1. A planar electrode having a multiplicity of microelectrodes for measurement of electric activities of nerve cells, comprising an electrode section having a multiplicity of microelectrodes insulated from each other and each connectable to outside said electrode section, said microelectrodes each having an area from $4 \times 10^2$ $\mu m^2$ to $4 \times 10^4$ $\mu m^2$, wherein said microelectrodes have an impedance in the range of 1 Ω to 100 kΩ when said electrode section is covered with an electrolyte solution and an alternating voltage of 1 kHz, 50 mV is provided to a reference electrode between said electrolyte solution and said microelectrodes.

2. The planar electrode of claim 1 wherein each of said microelectrodes has a coating thereon.

3. The planar electrode of claim 2 wherein each of said microelectrodes is comprised of an indium tin oxide alloy, covered thereon with at least one metal selected from the group consisting of Ag, Al, Bi, Au, Cu, Cr, Co, and Ni, and coated thereon with a metal containing platinum.

4. The planar electrode of claim 2 wherein each of said microelectrodes is comprised of an indium tin oxide alloy, covered thereon with Au and Ni, and coated thereon with a metal containing platinum.

5. The planar electrode of claim 2 wherein the multiplicity of microelectrodes are spaced apart with a microelectrode-to-microelectrode distance in the range of 10 $\mu$m to 1000 $\mu$m.

6. The planar electrode of claim 2 wherein a solution holding section for holding a cell culture liquid medium surrounds said electrode section.

7. The planar electrode of claim 2 wherein the multiplicity of microelectrodes are arranged in an 8×8 lattice.

8. The planar electrode of claim 2 wherein said impedance is in the range of 1 kΩ to 60 kΩ when an alternating voltage of 1 kHz, 50 mV is provided to a reference electrode between said electrolyte solution and said microelectrodes.

* * * * *